US00PP22761P2

(12) United States Plant Patent
Kolster

(10) Patent No.: US PP22,761 P2
(45) Date of Patent: May 29, 2012

(54) ***POTENTILLA* PLANT NAMED 'WHITE LADY'**

(50) Latin Name: *Potentilla fruticosa*
Varietal Denomination: White Lady

(75) Inventor: Pieter Kolster, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 195 days.

(21) Appl. No.: 12/799,431

(22) Filed: Apr. 23, 2010

(51) Int. Cl.
*A01H 5/00* (2006.01)

(52) U.S. Cl. ..... Plt./237

(58) Field of Classification Search ..... Plt./237
See application file for complete search history.

*Primary Examiner* — Wendy C Haas
(74) *Attorney, Agent, or Firm* — C. A. Whealy

(57) ABSTRACT

A new and distinct cultivar of *Potentilla* plant named 'White Lady', characterized by its upright and outwardly spreading plant habit; freely branching habit; large white-colored flowers; long flowering period; and good garden performance.

2 Drawing Sheets

Botanical designation: *Potentilla fruticosa.*
Cultivar denomination: 'WHITE LADY'.

BACKGROUND OF THE INVENTION

The present invention relates to a new and distinct cultivar of *Potentilla* plant, botanically known as *Potentilla fruticosa*, and hereinafter referred to by the name 'White Lady'.

The new *Potentilla* plant is a product of a planned breeding program conducted by the Inventor in Boskoop, The Netherlands. The objective of the breeding program was to develop new long-flowering *Potentilla* plants with attractive flower color.

The new *Potentilla* plant originated from a self-pollination in July, 2004 of *Potentilla fruticosa* 'Abbotswood', not patented. The new *Potentilla* plant was discovered and selected by the Inventor in August, 2005 as a flowering plant within the progeny of the stated self-pollination in a controlled environment in Boskoop, The Netherlands.

Asexual reproduction of the new *Potentilla* plant by vegetative cuttings in a controlled environment in Boijl, The Netherlands since June, 2006, has shown that the unique features of this new *Potentilla* plant are stable and reproduced true to type in successive generations.

SUMMARY OF THE INVENTION

Plants of the new *Potentilla* have been observed under all possible cultural and environmental conditions. The phenotype may vary somewhat with variations in cultural practices and environment such as temperature and light intensity without, however, any variance in genotype.

The following traits have been repeatedly observed and are determined to be the unique characteristics of 'White Lady'. These characteristics in combination distinguish 'White Lady' as a new and distinct *Potentilla* plant:

1. Upright and outwardly spreading plant habit.
2. Freely branching habit.
3. Large white-colored flowers.
4. Long flowering period.
5. Good garden performance.

Plants of the new *Potentilla* can be compared to plants of the parent, 'Abbotswood'. Plants of the new *Potentilla* differ primarily from plants of 'Abbotswood' in the following characteristics:

1. Plants of the new *Potentilla* are more compact than plants of 'Abbotswood'.
2. Leaves of plants of the new *Potentilla* are pubescent whereas leaves of plants of 'Abbotswood' are glabrous.
3. In The Netherlands, plants of the new *Potentilla* flower until November whereas plants of 'Abbotswood' flower until mid-September.

Plants of the new *Potentilla* can be compared to plants of *Potentilla fruticosa* 'Red Lady', disclosed in a U.S. Plant patent application Ser. No. 12/799,431. Plants of the new *Potentilla* differ primarily from plants of 'Red Lady' in flower color as plants of 'Red Lady' have red-colored flowers.

BRIEF DESCRIPTION OF THE PHOTOGRAPHS

The accompanying colored photographs illustrate the overall appearance of the new *Potentilla* plant, showing the colors as true as it is reasonably possible to obtain in colored reproductions of this type. Colors in the photographs may differ slightly from the color values cited in the detailed botanical description which accurately describe the colors of the new *Potentilla* plant.

The photograph on the first sheet comprises a side perspective view of a typical flowering plant of 'White Lady' grown in a container.

The photograph at the top of the second sheet is a close-up view of typical leaves and stems of 'White Lady'.

The photograph at the bottom of the second sheet is a close-up view of typical flowering stems of 'White Lady'.

DETAILED BOTANICAL DESCRIPTION

The aforementioned photographs and following observations, measurements and values describe plants grown in two-liter containers during the autumn in an outdoor nursery in Boskoop, The Netherlands and under conditions which closely approximate commercial *Potentilla* production. During the production of the plants, day temperatures ranged from 8° C. to 18° C. and night temperatures ranged from 1° C.

to 12° C. Plants were two years old when the photographs and the description were taken. In the description, color references are made to The Royal Horticultural Society Colour Chart, 2007 Edition, except where general terms of ordinary dictionary significance are used.

Botanical classification: *Potentilla fruticosa* 'White Lady'.

Parentage: Self-pollination of *Potentilla fruticosa* 'Abbotswood', not patented.

Propagation:

*Type*.—By vegetative cuttings.

*Time to initiate roots*.—About 14 days at 20° C.

*Time to develop roots*.—About 40 days at 20° C.

*Root description*.—Fine, fibrous; brown in color.

*Rooting habit*.—Freely branching.

Plant description:

*Plant form and growth habit*.—Perennial deciduous shrub; upright and outwardly spreading plant habit, roughly globular in shape; moderately vigorous growth habit.

*Branching habit*.—Freely branching habit, usually about 21 lateral branches develop per plant; pinching enhances lateral branch development.

*Plant height*.—About 29.6 cm.

*Plant diameter* (*area of spread*).—About 40.3 cm.

Lateral branch description:

*Length*.—About 12.6 cm.

*Diameter*.—About 1.2 mm.

*Internode length*.—About 1.4 cm.

*Strength*.—Strong.

*Texture*.—Pubescent, rough; woody with development.

*Color, developing*.—Close to 181A to 181B.

*Color, woody*.—Between 174A and 177A.

Foliage description:

*Arrangement*.—Alternate; palmately compound with three leaflets per leaf; leaflets sessile.

*Leaf length*.—About 2.9 cm.

*Leaf width*.—About 3.3 cm.

*Leaflet length*.—About 1.9 cm.

*Leaflet width*.—About 1.4 cm.

*Leaflet shape*.—Narrowly obovate to elliptic.

*Leaflet apex*.—Short apiculate.

*Leaflet base*.—Attenuate.

*Leaflet margin*.—Entire.

*Leaflet texture, upper and lower surfaces*.—Sparsely pubescent.

*Leaflet venation pattern*.—Pinnate.

*Leaflet color*.—Developing leaves, upper surface: Close to N137C. Developing leaves, lower surface: Close to 138B. Mature leaves, upper surface: Close to 137A; venation, close to N137B. Mature leaves, lower surface: Close to 148C; venation, close to 148C to 148D.

*Leaf petiole*.—Length: About 1.2 cm. Diameter: About 0.75 mm. Texture, upper and lower surfaces: Smooth, glabrous. Color, upper and lower surfaces: Close to 144B to 144C.

Flower description:

*Flower arrangement, shape and habit*.—Single rotate flowers, flowers usually terminal and sometimes in pairs; flowers face upright; freely flowering habit, about six flowers and flower buds per lateral branch.

*Fragrance*.—None detected.

*Natural flowering season*.—Plants begin flowering about 7.5 months after planting and flower from the late spring into the late autumn in The Netherlands.

*Flower longevity on the plant*.—About five days; flowers not persistent.

*Flower buds*.—Length: About 8 mm. Diameter: About 5 mm. Shape: Ovate. Color: Close to 150B; apex, close to 144A.

*Flowers*.—Diameter: About 3.1 cm. Depth (height): About 9 mm.

*Petals*.—Arrangement: Five in a single whorl. Length: About 1.4 cm. Width: About 1.3 cm. Shape: Orbicular; slightly concave. Apex: Obtuse. Base: Attenuate. Margin: Entire. Texture, upper and lower surfaces: Smooth, glabrous. Color: When opening, upper and lower surfaces: Close to NN155B. Fully opened, upper and lower surfaces: Close to NN155B.

*Petaloids*.—None observed.

*Sepals*.—Arrangement: Five in a single whorl. Length: About 8 mm. Width: About 3 mm. Shape: Ovate. Apex: Acute. Base: Broadly cuneate. Margin: Entire. Texture, upper and lower surfaces: Smooth, glabrous. Color: Immature and mature, upper surface: Close to 150B; apex, close to 144A. Immature and mature, lower surface: Close to 145A; apex, close to 144A.

*Pedicels*.—Strength: Moderately strong. Length: About 2.5 cm. Diameter: About 1 mm. Aspect: Erect. Texture: Smooth, glabrous. Color: Close to 145B.

*Reproductive organs*.—Stamens: Quantity per flower: About 30. Filament length: About 2 mm. Anther size: About 1 mm by 0.5 mm. Anther shape: Ovate. Anther color: Close to 10C. Pollen amount: Scarce. Pollen color: Close to 14A. Pistils: Quantity per flower: About 30. Pistil length: About 2 mm. Stigma color: Close to 3A. Style length: About 1 mm. Style color: Close to 3B to 3C. Ovary color: Close to 144B to 144C.

Temperature tolerance: Plants of the new *Potentilla* have been observed to be hardy to USDA Hardiness Zone 3 and to tolerate high temperatures of about 40° C.

Pathogen/pest resistance: Plants of the new *Potentilla* have not been shown to be resistant to pathogens and pests common to *Potentilla*.

It is claimed:

1. A new and distinct *Potentilla* plant named 'White Lady' as illustrated and described.

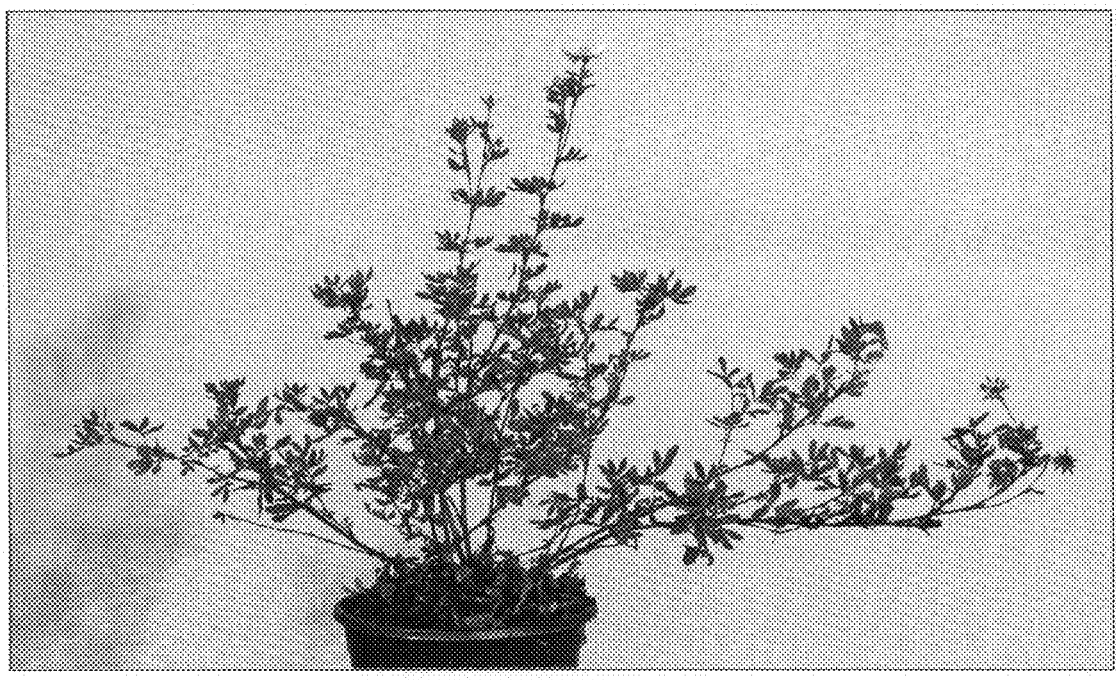

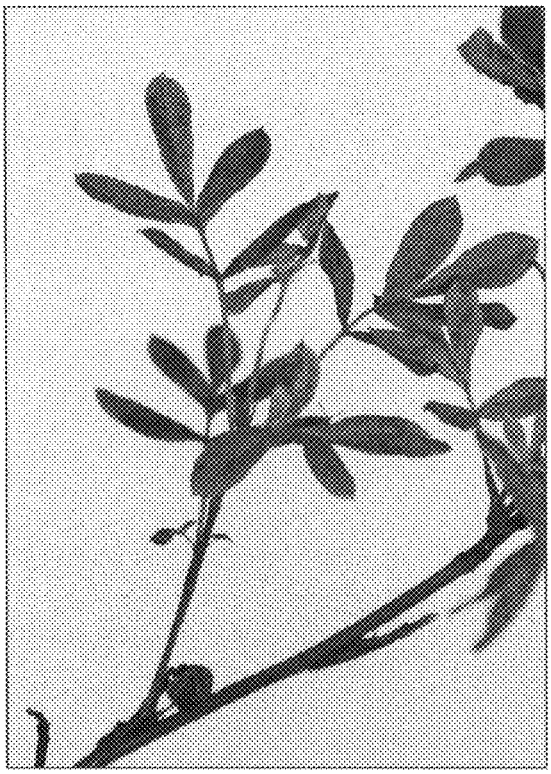
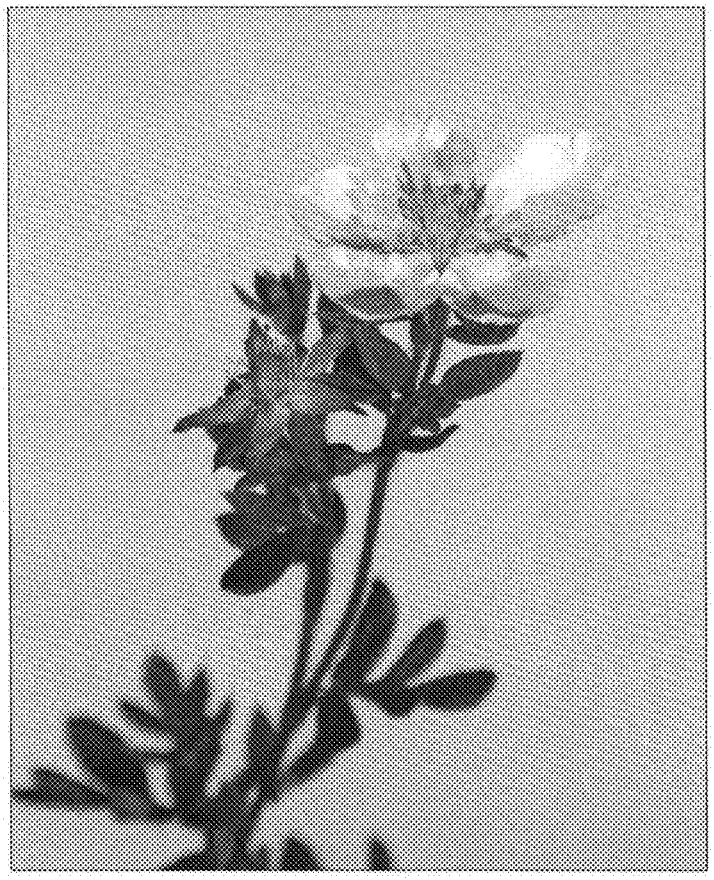

* * * * *